(12) United States Patent
Akkurt (10) Patent No.: US 6,316,940 B1
(45) Date of Patent: Nov. 13, 2001

(54) SYSTEM AND METHOD FOR IDENTIFICATION OF HYDROCARBONS USING ENHANCED DIFFUSION

(75) Inventor: Ridvan Akkurt, Kingwood, TX (US)

(73) Assignee: Numar Corporation, Malvern, PA (US)

( * ) Notice: Subject to any disclaimer, the term of this patent is extended or adjusted under 35 U.S.C. 154(b) by 0 days.

(21) Appl. No.: 09/270,616

(22) Filed: Mar. 17, 1999

(51) Int. Cl.$^7$ ................................................. F01V 3/00
(52) U.S. Cl. .............................................................. 324/303
(58) Field of Search ............................................. 324/303

(56) References Cited

U.S. PATENT DOCUMENTS

| Re. 32,913 | 4/1989 | Clark ..................................... 324/338 |
| 1,158,959 | 11/1915 | Beach . |
| 2,912,641 | 11/1959 | Ruble . |
| 2,973,471 | 2/1961 | Armistead et al. . |
| 3,205,477 | 9/1965 | Kalbfell . |
| 3,213,357 | 10/1965 | Brown et al. . |
| 3,360,716 | 12/1967 | Bloom et al. . |
| 3,395,337 | 7/1968 | Varian . |
| 3,402,344 | 9/1968 | Brown et al. . |
| 3,453,433 | 7/1969 | Alger et al. .......................... 250/83.3 |
| 3,508,438 | 4/1970 | Alger et al. ............................. 73/152 |
| 3,567,935 | 3/1971 | Nagel .................................. 250/83.1 |
| 3,567,936 | 3/1971 | Tittman ............................... 250/83.1 |
| 3,590,228 | 6/1971 | Burke ............................... 235/151.35 |
| 3,593,116 | 7/1971 | Culpepper ................................ 324/5 |

(List continued on next page.)

FOREIGN PATENT DOCUMENTS

| 0 581 666 A3 | 2/1994 | (EP) . |
| 0 649 035 B1 | 4/1995 | (EP) . |
| WO 96/12976 | * 5/1996 | (WO) . |
| WO 97/14063 | * 4/1997 | (WO) . |
| WO 99/47939 | * 3/1999 | (WO) . |
| WO 00/26696 | * 5/2000 | (WO) . |

OTHER PUBLICATIONS

Castleman, Kenneth P. "Digital Image Processing" textbook pp. 452–462 1996 no month.*
Gonzalez, Rafael C. and Woods, Richard E. "Digital Image Processing" textbook pp. 443–457 no month 1992.*
International Publication No. WO 98/25164, Publication Date Jun. 11, 1998; from International Application No. PCT/US97/21889, Filed Nov. 26, 1997; Priority Data: Serial No. 08/759,829, Filed Dec. 4, 1996.
Morriss et al., "Hydrocarbon Saturation and Viscosity Estimation from NMR Loggin in the Belridge Diatomite," 35th SPWLA Annual Loggin Symposium (Jun. 19–22, 1994), pp. 1–24.
Carr et al., "Effects of Diffusion on Free Precision in Nuclear Magnetic Resonance Experiments," *Physical Review*, vol. 94, No. 3 (May 1, 1954), pp. 630–638.
Schlumberger Wireline & Testing, "Combinable Magnetic Resonance tool reliably indicates water–free production and reveals hard–to–find pay zones," (Jun. 1995).

(List continued on next page.)

*Primary Examiner*—Jay Patidar
*Assistant Examiner*—Tiffany A. Fetzner
(74) *Attorney, Agent, or Firm*—Pennie & Edmonds LLP (57) ABSTRACT

A novel method and system is disclosed for the separation of fluid phases in NMR borehole measurements. The method is based on forcing diffusion as the dominant relaxation mechanism for certain fluid phase by adjusting certain user controlled parameters. The invention is more specifically applicable to separation of brine from hydrocarbons, using enhanced diffusion to establish an upper limit for the $T_2$ spectral distribution of the brine. Parameters that can be modified to enhance the diffusion relaxation during the measurements include the interecho spacing $T_E$ and the magnetic field gradient G of the measurement tool.

27 Claims, 7 Drawing Sheets

U.S. PATENT DOCUMENTS

| | | | |
|---|---|---|---|
| 3,617,867 | 11/1971 | Herzog | 324/5 |
| 3,638,484 | 2/1972 | Tixier | 73/152 |
| 3,657,730 | 4/1972 | Robinson et al. | 324/5 |
| 3,667,035 | 5/1972 | Slichter | 324/5 R |
| 3,777,560 | 12/1973 | Guignard | 73/151.5 |
| 3,784,898 | 1/1974 | Darley et al. | 324/5 R |
| 3,896,668 | 7/1975 | Anderson et al. | 73/152 |
| 4,291,271 | 9/1981 | Lauffer | 324/307 |
| 4,310,887 | 1/1982 | Suau | 364/422 |
| 4,528,508 | 7/1985 | Vail, III | 324/303 |
| 4,686,364 | 8/1987 | Herron | 250/256 |
| 4,710,713 | 12/1987 | Taicher et al. | 324/303 |
| 4,717,876 | 1/1988 | Masi et al. | 324/303 |
| 4,717,877 | 1/1988 | Taicher et al. | 324/303 |
| 4,717,878 | 1/1988 | Taicher et al. | 324/303 |
| 4,728,892 | 3/1988 | Vinegar et al. | 324/309 |
| 4,885,540 | 12/1989 | Snoddy et al. | 324/318 |
| 4,933,638 | 6/1990 | Kenyon et al. | 324/303 |
| 4,994,777 | 2/1991 | Leupold et al. | 335/302 |
| 5,023,551 | 6/1991 | Kleinberg et al. | 324/303 |
| 5,055,787 | 10/1991 | Kleinberg et al. | 324/303 |
| 5,055,788 | 10/1991 | Kleinberg et al. | 324/303 |
| 5,122,746 | 6/1992 | King et al. | 324/307 |
| 5,212,447 | 5/1993 | Paltiel | 324/300 |
| 5,280,243 | 1/1994 | Miller | 324/303 |
| 5,309,098 | 5/1994 | Coates et al. | 324/303 |
| 5,349,184 | 9/1994 | Wraight | 250/266 |
| 5,350,925 | 9/1994 | Watson | 250/269.3 |
| 5,363,041 | 11/1994 | Sezginer | 324/303 |
| 5,376,884 | 12/1994 | Sezginer | 324/303 |
| 5,379,216 | 1/1995 | Head | 364/422 |
| 5,381,092 | 1/1995 | Freedman | 324/303 |
| 5,387,865 | 2/1995 | Jerosch-Herold et al. | 324/303 |
| 5,397,989 | 3/1995 | Spraul et al. | 324/321 |
| 5,412,320 | 5/1995 | Coates | 324/303 |
| 5,432,446 | 7/1995 | Macinnis et al. | 324/303 |
| 5,453,692 | 9/1995 | Takahashi et al. | 324/318 |
| 5,486,761 | 1/1996 | Sezginer | 324/303 |
| 5,486,762 | 1/1996 | Freedman et al. | 324/303 |
| 5,497,087 | 3/1996 | Vinegar et al. | 324/303 |
| 5,498,960 | 3/1996 | Vinegar et al. | 324/303 |
| 5,517,115 | 5/1996 | Prammer | 324/303 |
| 5,557,200 | 9/1996 | Coates | 324/303 |
| 5,557,201 | 9/1996 | Kleinberg et al. | 324/303 |
| 5,565,775 | 10/1996 | Stallmach et al. | 324/303 |
| 5,629,623 | 5/1997 | Sezginer et al. | 324/303 |
| 5,680,043 | 10/1997 | Hurlimann et al. | 324/303 |
| 5,705,927 | 1/1998 | Sezginer et al. | 324/303 |
| 5,796,252 | 8/1998 | Kleinberg et al. | 324/303 |
| 5,936,405 | * 8/1999 | Prammer et al. | 324/303 |
| 6,005,389 | * 12/1999 | Prammer et al. | 324/303 |
| 6,229,308 | * 5/2001 | Freedman | 324/303 |

OTHER PUBLICATIONS

Morriss et al., "Field Test of an Experimental Pulsed Nuclear Magnetism Tool," SPWLA Annual Logging Symposium (Jun. 13–16, 1993), pp. 1–23.

Coates et al., "Core Data and the MRIL Show—A New Approach to 'Formation Factor,'" National SPWLA Convention (Jun. 15, 1992), pp. 1–15.

Kleinberg et al., "Novel NMR Apparatus for Investigating an External Sample," *Journal of Magnetic Resonance*, (1992) pp. 466–485.

Coates et al., "An Investigation of a New Magnetic Resonance Imaging Log," National SPWLA Convention (Jun. 18, 1991), pp. 1–24.

Howard et al., "Proton Magnetic Resonance and Pore–Size Variations in Reservoir Sandstones," *Society of Petroleum Engineers*(1990), pp. 733–741.

Miller et al., "Spin Echo Magnetic Resonance Logging: Porosity and Free Fluid Index Determination," *Society of Petroleum Engineers*(1990), pp. 321–334.

Kenyon et al., "Pore–Size Distribution and NMR in Microporous Cherty Sandstones," SPWLA Thirtieth Annual Logging Symposium (Jun. 11–14, 1989), pp. 1–24.

Schlumberger Technology News—Oilfield Bulletin, "Fifth Generation Nuclear Magnetic Resonance Logging Tool: A Major Advance in Producibility Measurement Technology," (Jul. 1995) (2 pp.).

Akkurt et al., "NMR Logging of Natural Gas Reservoirs" SPWLA 35th Annual Logging Symposium (Jun. 26–29, 1995).

Prammer, M.G., "NMR Pore Size Distributions and Permeability at the Well Site," *Society of Petroleum Engineers*(Sep. 25, 1995) pp. 55–64.

Chandler et al., "Improved Log Quality with a Dual–Frequency Pulsed NMR Tool," *Society of Petroleum Engineers*(1994) pp. 23–35.

Straley et al., "NMR in Partially Saturated Rocks: Laboratory Insights on Free Fluid Index and Comparison with Borehole Logs," SPWLA Annual Logging Symposium (Jun. 27, 1991) pp. 40–56.

Gallegos et al., "A NMR Technique for the Analysis of Pore Structure: Determination of Continuous Pore Size Distributions," Journal of Colloid and Interface Science, vol. 122, No. 1, Mar. 1988, pp. 143–153.

Gallegos et al., "NMR Tecnique for the Analysis of Pore Structure: Application to Materials with Well–Defined Pore Structure," Journal of Colloid and Interface Science, vol. 119, No. 1, Sep. 1987, pp. 127–140.

Neuman et al., "Applications of Nuclear Magnetism Logging to Formation Evaluation," Journal of Petroleum Technology, vol. 34, (1982) pp. 2853–2862.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Jackson et al., "Western Gas Sands Project Los Alamos NMR Well Logging Tool Development," Los Alamos National Laboratory (Oct. 1981—Sep. 1982) pp. 1–28.

Clavier et al., "The Theoretical and Experimental Bases for the 'Dual Water' Model for the Interpretation of Shaly Sands," *Journal of Petroleum Technology* (Apr. 1984), pp. 3–15.

Petrakis et al., "The Utilization of Nuclear Magnetic Resonance Spectroscopy for Petroleum, Coal, Oil Shale, Petrochemicals, and Polymers. Phenomenology, Paradigms of Applications, and Instrumentation," 594 Applied Spectroscopy Reviews vol. 15 (1979) No. 2, pp. 195–260.

Brownstein et al., "Importance of classical diffusion in NMR studies of water in biological cells," The American Physical Society, vol. 19, No. 6, (1979) pp. 2446–2453.

Farrar et al., "Pulse and Fourier Transform NMR Introduction to Theory and Methods," Academic Press (1971) pp. 26–29.

Waxman et al., "Electrical Conductives in Oil–Bearing Shaly Sands," *Society of Petroleum Engineers Journal*(1968) pp. 107–122.

Brown et al., "Nuclear Magnetism Logging," Transactions of the American Institute of Mining, Metallurgical, and Petroleum Engineers, vol. 219 (1960), pp. 199–207.

* cited by examiner

LOG EXAMPLE 1

LOG EXAMPLE 2, TRACK DEFINITIONS ARE THE SAME AS IN 1.

SYSTEM AND METHOD FOR IDENTIFICATION OF HYDROCARBONS USING ENHANCED DIFFUSION

FIELD OF THE INVENTION

The present invention relates to nuclear magnetic resonance (NMR) borehole measurements and more particularly to separation of signals from different fluids using user-adjusted measurement parameters.

BACKGROUND

One of the main issues in examining the petrophysical properties of a geologic formation is the ability of the measuring device to differentiate between individual fluid types. For example, in the search for oil it is important to separate signals due to producible hydrocarbons from the signal contribution of brine, which is a fluid phase of little interest. However, so far no approach has been advanced to reliably perform such fluid separation.

Various methods exist for performing measurements of petrophysical parameters in a geologic formation. Nuclear magnetic resonance (NMR) logging, which is the focus of this invention, is among the best methods that have been developed for a rapid determination of such parameters, which include formation porosity, composition of the formation fluid, the quantity of movable fluid, permeability among others. At least in part this is due to the fact that NMR measurements are environmentally safe and are unaffected by variations in the matrix mineralogy.

To better appreciate how NMR logging can be used for fluid signal separation, it is first necessary to briefly examine the type of parameters that can be measured using NMR techniques. NMR logging is based on the observation that when an assembly of magnetic moments, such as those of hydrogen nuclei, are exposed to a static magnetic field they tend to align along the direction of the magnetic field, resulting in bulk magnetization. The rate at which equilibrium is established in such bulk magnetization upon provision of a static magnetic field is characterized by the parameter $T_1$, known as the spin-lattice relaxation time. Another related and frequently used NMR logging parameter is the spin-spin relaxation time $T_2$ (also known as transverse relaxation time), which is an expression of the relaxation due to non-homogeneities in the local magnetic field over the sensing volume of the logging tool. Both relaxation times provide information about the formation porosity, the composition and quantity of the formation fluid, and others.

Another measurement parameter obtained in NMR logging is the diffusion of fluids in the formation. Generally, diffusion refers to the motion of atoms in a gaseous or liquid state due to their thermal energy. Self-diffusion is inversely related to the viscosity of the fluid, which is a parameter of considerable importance in borehole surveys. In a uniform magnetic field, diffusion has little effect on the decay rate of the measured NMR echoes. In a gradient magnetic field, however, diffusion causes atoms to move from their original positions to new ones, which moves also cause these atoms to acquire different phase shifts compared to atoms that did not move. This contributes to a faster rate of relaxation.

NMR measurements of these and other parameters of the geologic formation can be done using, for example, the centralized MRIL® tool made by NUMAR, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Millen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994. Details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115, 5,557,200 and 5,696,448, all of which are commonly owned by the assignee of the present invention. The Schlumberger CMR tool is described, for example, in U.S. Pat. Nos. 5,055,787 and 5,055,788 to Kleinberg et al. and further in "Novel NMR Apparatus for Investigating an External Sample," by Kleinberg, Sezginer and Griffin, J. Magn. Reson. 97, 466–485, 1992. The content of the above patents and publications is hereby expressly incorporated by reference.

It has been observed that the mechanisms which determine the measured values of $T_1$, $T_2$ and diffusion depend on the molecular dynamics of the formation being tested and on the types of fluids present. Thus, in bulk volume liquids, which typically are found in large pores of the formation, molecular dynamics is a function of both molecular size and inter-molecular interactions, which are different for each fluid. Water, gas and different types of oil each have different $T_1$, $T_2$ and diffusivity values. On the other hand, molecular dynamics in a heterogeneous media, such as a porous solid that contains liquid in its pores, differs significantly from the dynamics of the bulk liquid, and generally depends on the mechanism of interaction between the liquid and the pores of the solid media. It will thus be appreciated that a correct interpretation of the measured signals can provide valuable information relating to the types of fluids involved, the structure of the formation and other well-logging parameters of interest.

Figure 4A:
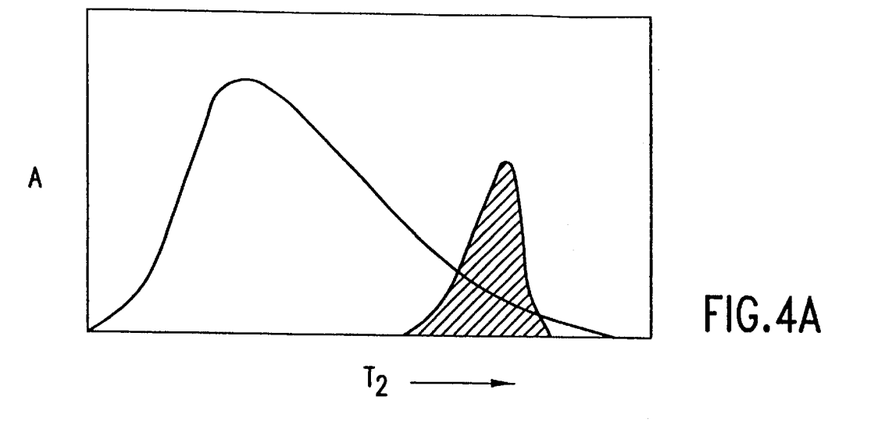
Figure 4B:
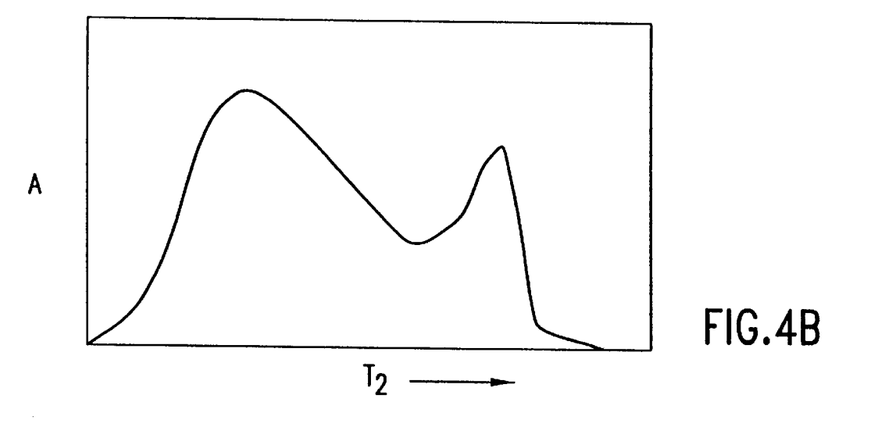

One problem encountered in standard NMR measurements is that in some cases signals from different fluid phases cannot be fully separated. For example, NMR signals due to brine, which is of no interest to oil production, cannot always be separated from signals due to producible hydrocarbons. The reason is that there is an overlap in the spectra of the measured signals from these fluids (see, for example, FIGS. 4a and 4b showing this overlap in the case of standard brine and hydrocarbon $T_2$ amplitude spectra).

Several methods for acquiring and processing gradient NMR well log data have been proposed recently that enable the separation of different fluid types. These separation methods are based primarily on the existence of a $T_1$ contrast and a diffusion contrast in NMR measurements of different fluid types. Specifically, a $T_1$ contrast is due to the fact that light hydrocarbons have long $T_1$, times, roughly 1 to 3 seconds, whereas $T_1$ values longer than 1 second are unusual for water-wet rocks. In fact, typical $T_1$'s are much shorter than 1 sec, due to the typical pore sizes encountered in sedimentary rocks, providing an even better contrast.

Diffusion in gradient magnetic fields provides a separate contrast mechanism applicable to $T_2$ measurements that can be used to further separate the long $T_1$ signal discussed above into its gas and oil components. In particular, at reservoir conditions the self-diffusion coefficient $D_0$ of gases, such as methane, is at least 50 times larger than that of water and light oil, which leads to proportionately shorter $T_2$ relaxation times associated with the gas. Since diffusion has no effect on the $T_1$ measurements, the resulting diffusion contrast can be used to separate oil from gas.

The $T_1$ and diffusion contrast mechanisms have been used to detect gas and separate different fluid phases in what is known as the differential spectrum method (DSM) proposed first in 1995. The original DSM uses two standard single-echo spacing logs acquired at different wait times in two separate passes. The short wait time $T_{WS}$ is chosen large enough to allow full recovery of the brine signal, i.e., $T_{WS} > 3 \max(T_{1,water})$, while the long wait time $T_{WL}$ is selected such that $T_{WL} > T_1$ of the light hydrocarbon, usually assumed to be gas. At each depth, the differential spectrum is formed by subtracting the $T_2$ distribution measured at $T_{WS}$ from the one measured at $T_{WL}$. Because $T_1$ recovery of the water signal is essentially complete at both wait times, this signal is eliminated following the substraction, and the differential spectrum is therefore due only to a hydrocarbon signal. While the DSM method has been applied successfully for the detection of gas and the separation of light hydrocarbons, there are several problems associated with it that have not been addressed adequately in the past.

First, DSM requires a logging pass associated with relatively long wait times ($T_W$ approximately 10 sec). Accordingly, DSM-based logging is by necessity relatively slow.

DSM's use of $T_1$ contrast may cause additional problems. For example, the required $T_1$ contrast may disappear in wells drilled with water-based mud, even if the reservoir contains light hydrocarbons. This can happen because water from the mud invades the big pores first, pushing out the oil and thus adding longer $T_2$'s to the measurement spectrum. In such cases, DSM or standard NMR time domain analysis (TDA) methods have limited use either because there is no separation in the $T_2$ domain, or because the two phases are too close and can not be picked robustly.

Separation problems similar to the one described above can also occur in carbonate rocks. In carbonates an overlap between the brine and hydrocarbons phases is likely because the surface relaxivity in carbonates is approximately ⅓ that of sandstones. In other words, for the same pore size, the surface relaxation in carbonates is about 3 times longer than that for a sandstone, such weak surface relaxation causing an overlap between the observable fluid phases.

Additional problem for carbonates is the presence of vugs. Water bearing vugs, because of their large pore sizes, have long $T_2$'s and can easily be interpreted as oil by prior art techniques.

It is apparent, therefore, that there is a need for a new system and method for NMR borehole measurements in which these and other problems are obviated, and better separation is provided between NMR signals from producible oil and interfering signals from brine-type fluids.

SUMMARY OF THE INVENTION

The present invention is based on forcing diffusion as the dominant relaxation mechanism for the brine phase in NMR measurements of a geologic formation. To this end, in accordance with the present invention certain measurement parameters are changed as to enhance the role of diffusion relaxation in the brine phase. The enhanced diffusion relaxation in turn establishes an upper limit for the $T_2$ distribution of the brine phase, which limit can be calculated. Once this upper limit is found, any phase having a longer $T_2$ can be identified unambiguously as not being brine, i.e., as a hydrocarbon.

The measurement parameters which are varied in accordance with the present invention to establish an upper limit in the $T_2$ distribution of the brine phase are the inter echo time $T_E$ and the magnetic field gradient G of the tool. In addition to the $T_2$ spectral domain, in accordance with this invention the brine phase can be separated from hydrocarbons using time domain analysis techniques based on performing enhanced diffusion measurements.

In particular, in accordance with a preferred embodiment, a method for nuclear magnetic resonance measurements of the petrophysical properties of a geologic formation is disclosed, comprising the steps of: providing a set of NMR measurement parameters that establish an upper limit in the apparent transverse relaxation $T_{2A}$ of a brine phase of the formation; obtaining a pulsed NMR log using the provided set of measurement parameters; determining from the NMR log a distribution of transverse relaxation times; and estimating from the distribution of transverse relaxation times the contribution of the hydrocarbon phase as distinct from brine.

BRIEF DESCRIPTION OF THE DRAWINGS

The present invention will be understood and appreciated more fully from the following detailed description taken in conjunction with the drawings in which:

FIGS. 4(*a*–*c*) are $T_2$ plots that illustrate the separation of the brine phase using enhanced diffusion.

DETAILED DESCRIPTION

The System

Figure 1:
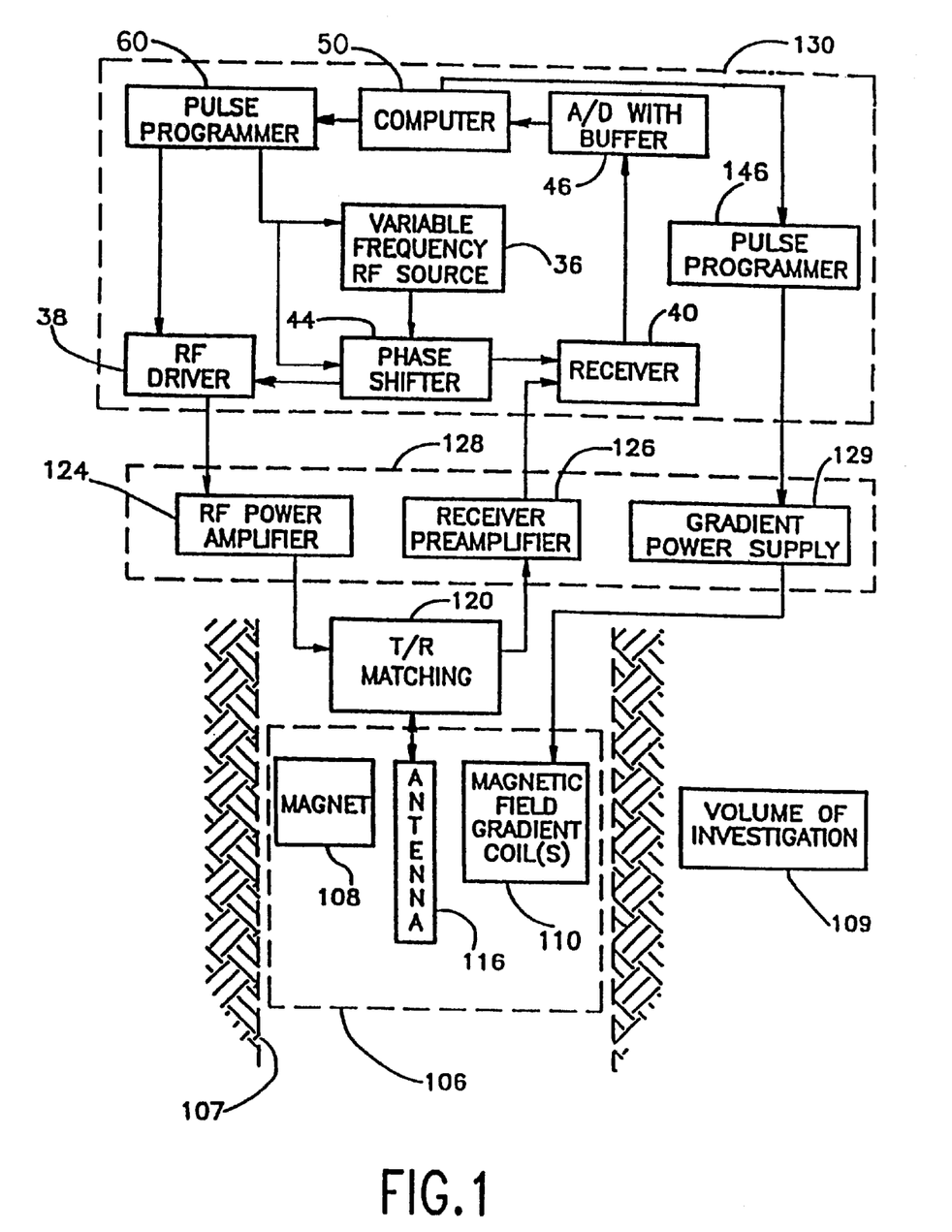
FIG. 1 is a partially pictorial, partially block diagram illustration of an apparatus for obtaining nuclear magnetic resonance (NMR) measurements in accordance with a preferred embodiment of the present invention.

Reference is first made to FIG. 1, which illustrates an apparatus constructed and operative in accordance with a preferred embodiment of the present invention for obtaining nuclear magnetic resonance (NMR) measurements. The apparatus includes a first portion 106, which is arranged to be lowered into a borehole 107 in order to examine the nature of materials in the vicinity of the borehole.

The first portion 106 comprises a magnet or a plurality of magnets 108, which preferably generate a substantially uniform static magnetic field in a volume of investigation 109 extending in the formation surrounding the borehole. The first portion 106 also comprises an RF antenna coil 116 which produces an RF magnetic field at the volume of investigation 109.

A magnetic field gradient coil, or plurality of coils, 110 generates a magnetic field gradient at the volume of investigation 109. This additional contribution to the magnetic field, which is essential for the enhanced diffusion method of the present invention, has a field direction preferably collinear with the substantially uniform field and has a substantially uniform magnetic field gradient. The magnetic field gradient may or may not be pulsed, i.e., switched on and off by switching the dc current flowing through the coil or coils 110. The magnet or magnets 108, antenna 116 and the gradient coil 110 constituting portion 106 are also referred to as a probe.

The antenna together with a transmitter/receiver (T/R) matching circuit 120, which typically includes a resonance capacitor, a T/R switch and both to-transmitter and to-receiver matching circuitry, are coupled to an RF power amplifier 124 and a receiver preamplifier 126. A gradient power supply 129 provides the dc current required for the magnetic field gradient generating coils 110. All the elements described above are normally contained in a housing 128 which is passed through the borehole. Alternatively, some of the above elements may be located above ground.

Indicated in a block 130 is control circuitry for the logging apparatus including a computer 50, which is connected to a pulse programmer 60 that controls the operation of a variable frequency RF source 36 as well as an RE driver 38. RF driver 38 also receives input from the variable frequency source 36 through a phase shifter 44, and outputs to RF power pre-amplifier 124.

The output of RF receiver amplifier 126 is supplied to an RF receiver 40 which receives an input from a phase shifter 44. Phase shifter 44 receives an input from variable frequency RF source 36. Receiver 40 outputs via an A/D converter with a buffer 46 to computer 50 for providing desired well logging output data for further use and analysis. Pulse programmer 146 controls the gradient coil power supply 129 enabling and disabling the flow of current, and hence the generation of static or pulsed field gradients, according to the commands of the computer 50. Some or all of the elements described hereinabove as being disposed in an above-ground housing, may instead be disposed below ground.

Figure 2:
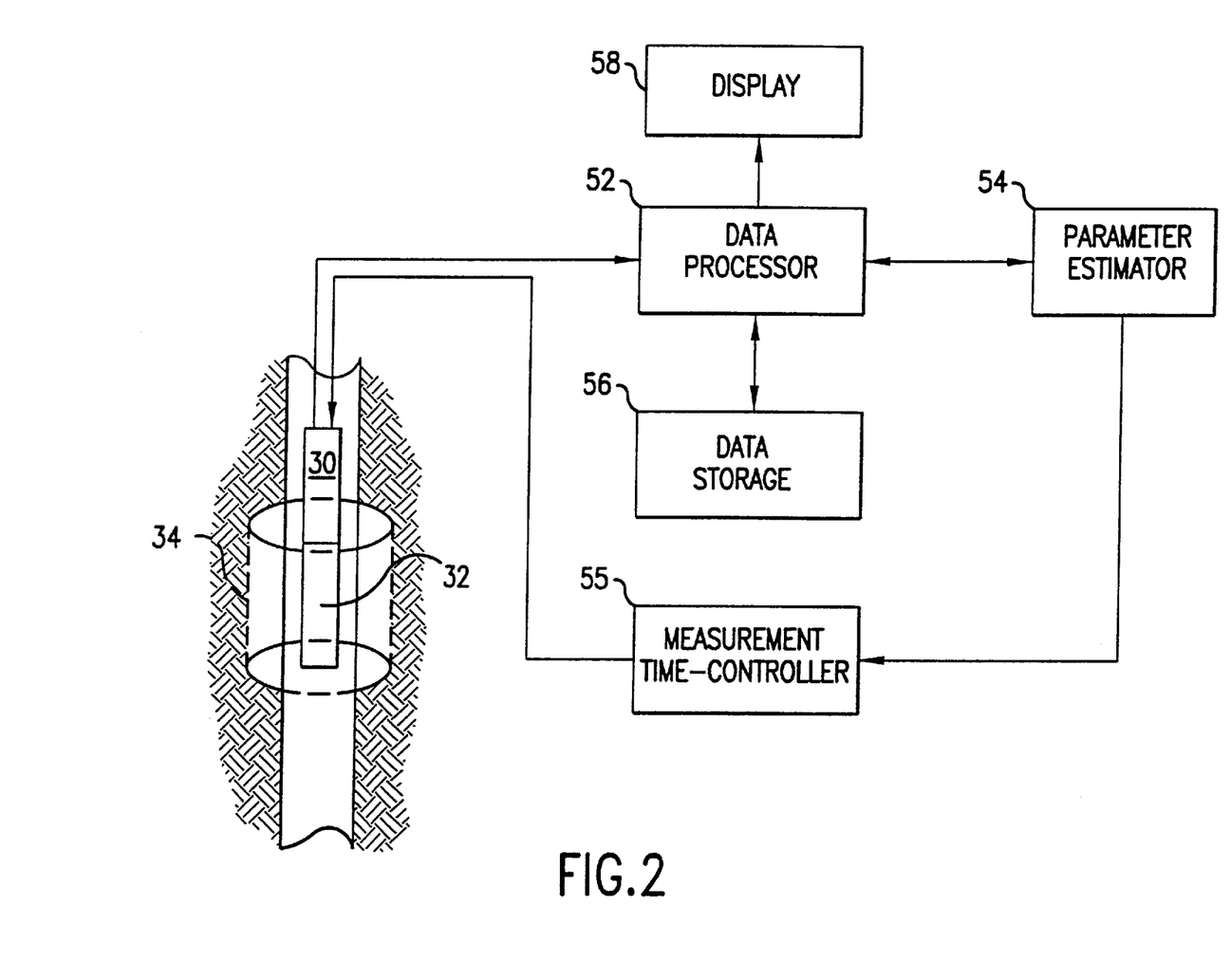
FIG. 2 is a block diagram of the system in accordance with a preferred embodiment which shows individual block components for controlling data collection, processing the collected data and displaying the measurement results.

FIG. 1 depicts a preferred embodiment of the system used in accordance with the present invention. Other systems may also be used in alternative embodiments. FIG. 2 is a block diagram of a generic system used in accordance with the present invention, and shows individual block components for controlling data collection, processing the collected data and displaying the measurement results. In FIG. 2 the tool's electronic section 30 comprises a probe controller and pulse echo detection electronics 32. The output signal from the detection electronics is processed by data processor 52 to analyze the relaxation characteristics of the material being investigated in the volume of investigation 34. The output of the data processor 52 is provided to the parameter estimator 54. Measurement time controller 55 provides an appropriate control signal to the probe. The processed data from the log measurement is stored in data storage 56. Data processor 52 is connected to display 58, which is capable of providing a graphical display of one or more measurement parameters, possibly superimposed on display data from data storage 56.

The components of the system of the present invention shown in FIG. 2 can be implemented in hardware or software, or any combination thereof suitable for practical purposes. Details of the structure, the operation and the use of logging tools, as illustrated in FIGS. 1 and 2 are also discussed, for example, in the description of the MRIL® tool to Numar Corporation, and in U.S. Pat. Nos. 4,717,876; 4,717,877; 4,717,878; 5,212,447; 5,280,243; 5,309,098; 5,412,320; 5,517,115, 5,557,200 and 5,696,448, and pending U.S. patent application Ser. No. 08/822,567 filed Mar. 19, 1997, the contents of which are incorporated herein for all purposes.

The Method

The present invention is based on forcing diffusion as the dominant relaxation mechanism for the brine phase in NMR measurements of a geologic formation. As known in the art, the main relaxation mechanisms that affect the $T_2$ relaxation times in rocks are molecular motion in fluids, surface relaxivity at the pore walls, and molecular diffusion in magnetic field gradients.

The first relaxation mechanism, known as bulk relaxation, is due to local motions, such as molecular tumbling and typically is observed in relatively large pores.

Bulk relaxation $T_{2B}$ for brine is on the order of several seconds and for the purposes of this invention is assumed to have negligible effect on the apparent $T_{2A}$ relaxation for the brine phase.

The second relaxation mechanism is surface relaxation at the pore walls. This relaxation mechanism is very significant in small pores and for fluid molecules, such as water, that wet the rock surfaces. This relaxation is generally much more rapid than the bulk relaxation—in the case of brine, the component $T_{2S}$ due to surface relaxation varies between submilliseconds to several hundreds of milliseconds.

The third relaxation mechanism is the diffusion of molecules in magnetic field gradients, such as those generated by Numar Corporation MRIL® tool. ordinarily, diffusion is a predominant relaxation mechanism only for gas.

The apparent $T_{2A}$ for brine is given by the expression:

$$\frac{1}{T_{2A}} = \frac{1}{T_{2S}} + \frac{1}{T_{2D}},$$

where $T_{2S}$ is associated with surface relaxation, $T_{2D}$ reflects the contribution of the diffusion relaxation mechanism and, as stated above, it is assumed that bulk relaxation for brine is negligible.

It can be readily appreciated that when $T_{2D}$ is much larger compared with $T_{2S}$, the contribution of the diffusion component in the above equation becomes negligible, and the expression for $T_{2A}$ collapses to the following approximation:

$$\frac{1}{T_{2A}} \approx \frac{1}{T_{2S}}.$$

Alternatively, however, under certain conditions which are described below, the contribution of the diffusion component $1/T_{2D}$ can be substantial, in which case it is simple to show that $$\max\{T_{2A}\} \leq T_{2D} \tag{1}$$

A closer examination of Eqn. (1) shows that if diffusion is forced to be the dominant relaxation mode, an upper limit of the apparent $T_{2A}$ relaxation of the brine phase can be established. Therefore, any fluid that has transverse relaxation time $T_2 > T_{2D}$ is not brine.

To see how this observation can be used in practical measurements to separate the contribution of different fluid phases, it is first noted that $T_{2D}$ is a function of the inter echo time $T_E$ used in the measurement, of the diffusion coefficient for water D, and the magnetic field gradient G generated by the measurement device. This function is given by the well known Carr-Purcell equation for the diffusion-induced relaxation $1/T_{2D}$:

$$T_{2D}^{-1} = \frac{D}{12}(\gamma \cdot G \cdot T_E)^2 \quad (2)$$

where $\gamma$ is the gyromagnetic ratio (=$2\pi \times 4258$ rad/sec/Gauss for protons).

The present invention is more specifically based on the observation that the inter echo spacing $T_E$ and the magnetic field gradient G are user-controlled parameters, so that by changing them the user can affect the dominant relaxation mode, forcing it to be of diffusion type. For this reason, the approach is referred to in this application as enhanced diffusion (ED). In particular, with reference to FIG. 1, the $T_E$ parameter can be modified by the pulse programmer 60. Furthermore, the gradient G is a function of the operating frequency, which is also user-adjustable. Therefore, by adjusting operator-controlled parameters of the NMR measurement, using the relationship expressed in Eqn. (2) one can establish an upper limit for the apparent relaxation $T_{2A}$ of the brine phase, so that the hydrocarbon signal can be isolated in the $T_2$ range.

Figure 3:
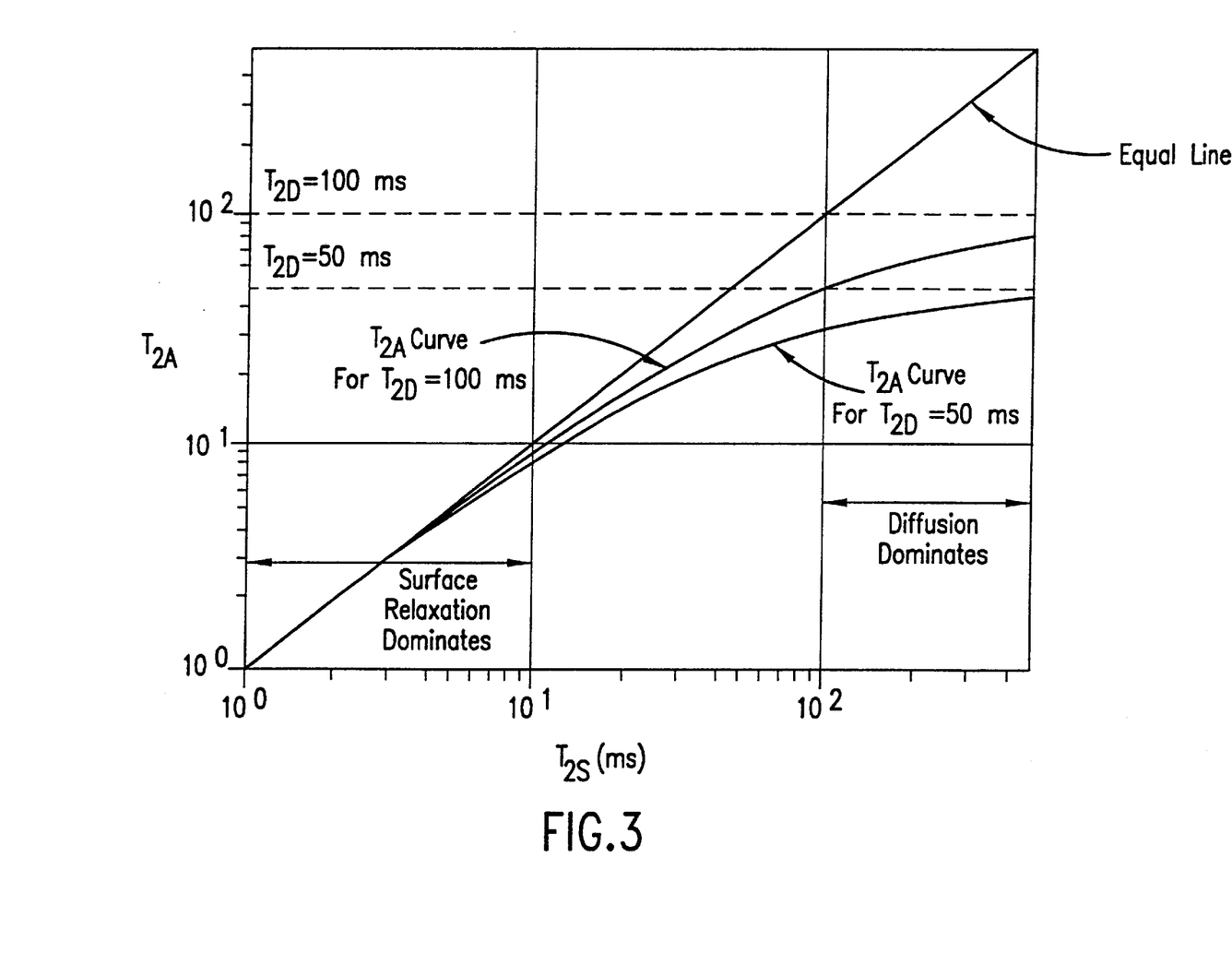
FIG. 3 illustrates the use of diffusion-dominated relaxation in accordance with the present invention to establish an upper limit in the apparent relaxation time $T_{2A}$ in a NMR measurement.

Specifically, as shown in FIG. 3, there are distinct areas where either surface relaxation or diffusion relaxation dominate the apparent $T_2$ relaxation. As expected, when surface relaxation is dominant, the apparent relaxation curve closely tracks the surface relaxation. On the other hand, when diffusion is the dominant relaxation mechanism, there is an upper limit to the apparent relaxation $T_{2A}$ of the brine. Importantly, this upper limit can be computed using Eqn. (2) above.

FIG. 3 shows two specific examples: the top curve is for the case when $T_{2D}$=100 ms; the bottom curve is for the case when $T_{2D}$=50 ms. In either case, the apparent $T_2$'s for brine are not longer than the imposed limit.

Accordingly, in the area where diffusion is the dominant relaxation mechanism for brine, an upper limit for the longest $T_2$ for the brine phase can be determined as a function of $T_E$, G, $D_W$, such that any phase with $T_2$'s longer than this upper limit is unambiguously identified as not being brine, i.e., as hydrocarbon. In practical applications, for diffusion to become a dominant mechanism, the inter echo spacing $T_E$ must be large, and the magnetic field gradient G must also be large.

FIG. 4 illustrates the separation of the brine and oil spectra in $T_2$ space in accordance with the present invention.

Figure 4C:
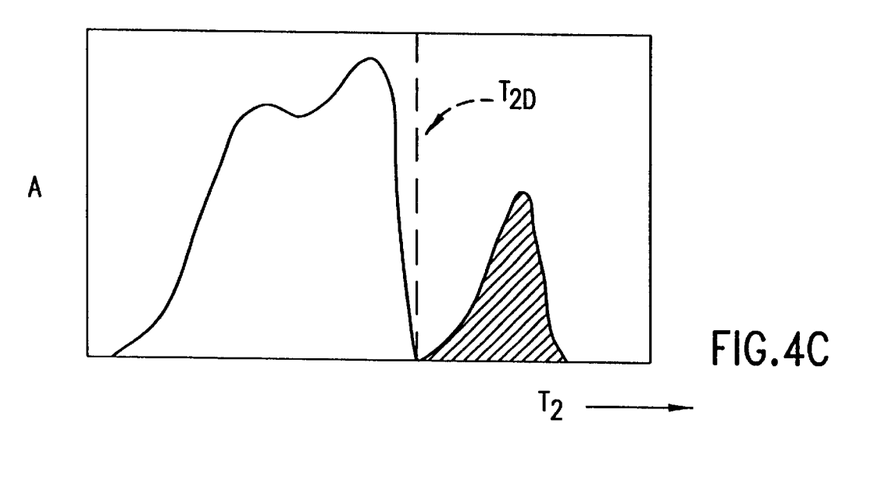

Specifically, FIG. 4a shows a typical brine and oil $T_2$ spectral distribution. FIG. 4b shows the $T_2$ spectrum when surface relaxation is dominant for brine. Although the $T_2$ spectrum is bi-modal, indicating the presence of two fluid phases, there is a clear area of overlap, so that the two fluid phases cannot be fully separated. Finally, FIG. 4c illustrates the case where all of the brine signal appears shorter than $T_{2D}$, clearly identifying the signal due to the hydrocarbon phase.

Although in the derivations above it has been assumed implicitly that enhanced diffusion measurements are made using single-value gradient, or for practical purposes a spike-type magnetic field gradient distribution, as is the case for the MRIL® tool, the approach can be extended easily to tools characterized by a wider gradient distribution, such as Schlumberger CMR tool. In such cases, in accordance with the present invention the $T_2$ limit is determined by the lowest G value for the gradient, because this value determines the longest $T_2$ due to diffusion.

More specifically, for gradient-distribution tools, assuming Gmin<G<Gmax, the upper limit of the apparent $T_{2A}$ for brine can be found using the expression:

$$\max(T_{2A}) = \frac{12}{D}(\gamma \cdot G_{min} \cdot T_E)^{-2} \quad (3)$$

which is obtained by rewriting Eqns. (1) and (2). Thus, it is clear that enhanced diffusion measurements can be performed using the CMR tool, even though some performance degradation can be expected due to the gradient distribution.

Two observations are in order for practical applications of the method of the present invention. First, for gradient-distribution tools the actual gradient of the magnetic field may go down to zero at certain locations. To avoid mathematical uncertainty, a non-zero value for $G_{min}$ is used in Eqn. (3), which value is selected from practical considerations including an understanding of the distribution of the magnetic field gradient of the tool.

Second, it should be understood that the upper limit in the apparent transverse relaxation $T_{2A}$ used in accordance with the present invention need not be a fixed number. Instead, this upper limit may take a range of values, and in a specific application can be determined from actual measurements parameters and various practical considerations. For example, in a specific embodiment of the method of the present invention, probabilities associated with a range of transverse relaxation values are assigned, and the selection of an actual upper limit value is refined on the basis of prior measurements and hypothesis testing.

Having described the enhanced diffusion (ED) approach underlying the present invention, it is instructive to compare it to the prior art, and to illustrate its operation in practical applications. In this regard, reference is made to the description of the differential spectrum method (DSM): Akkurt et al., "NMR logging of Natural Gas Reservoirs", paper N, presented at the 36th Annual Logging Symposium, Society of Professional Well Log Analysts, Paris, Jun. 26–29, 1995, and U.S. Pat. Nos. 5,497,087 and 5,498,960, the content of which publications is hereby incorporated by reference for all purposes.

a) NMR Signal Acquisition

In accordance with a preferred embodiment of the present invention a dual wait-time pulse sequence is run to collect the required NMR measurement data. Dual wait-time sequencing capability not requiring separate logging passes is provided by the MRIL® tool as described, for example, in co-pending application Ser. No. 08/822,567 assigned to the assignee of the present application, which is incorporated for all purposes. In alternative embodiments of the present invention, a single wait-time pulse sequence can also be used, since there will be $T_2$ separation between the two phases regardless of any $T_1$ contrast.

The inter echo times $T_E$ used in the enhanced-diffusion measurements of the present invention are longer compared with those used in standard DSM measurements (which typically are less than about 1.2 msec). Preferably, the $T_E$ parameter of the sequence is selected dependent on the temperature of the formation, the magnetic field gradient G generated by the tool (which is a function of the tool diameter, the temperature and the operating frequency for the tool), as well as the expected viscosity of the oil. Generally, the higher the expected oil viscosity, the longer the $T_E$.

The wait times $T_W$ used in accordance with the present invention are typically chosen between about 300 and 3000 milliseconds, but can be made substantially shorter because $T_1$ separation is not used, and therefore is not an issue in ED measurements. It should be noted that because the wait times $T_W$ for enhanced diffusion (ED) measurements in accordance with the present invention are much shorter compared to conventional DSM or time-domain analysis (TDA) applications (roughly about 3.5 seconds for ED compared to 11 seconds for DSM), logging speeds are much faster. This presents a significant advantage of the system and method of the present invention. It can be appreciated that because of the shorter wait times used by ED measurements, the method of the present invention can also result in increased vertical resolution at a given logging speed, because more data can be collected per unit length.

Additionally, the number of echoes acquired in ED measurements in accordance with the present invention is significantly smaller compared with that for conventional applications. In a specific embodiment, approximately about 150 echoes are acquired per CPMG sequence. This reduced number of echoes eases power requirements and allows easier operation of the tool, which features in turn provide additional advantages of the ED-based approach of the present invention.

b) Applications

The ED system and method of the present invention can be used instead of or in addition to standard NMR measurements in a number of practical situations. The method of the present invention is particularly well suited for applications where the $T_1$ contrast disappears or is reduced for some reason, and the standard DSM approach would fail.

For example, as noted above, in wells drilled with water-based mud $T_1$ contrast between brine and hydrocarbons may disappear, even if the reservoir contains light hydrocarbons. On the other hand, measurements conducted in accordance with the present invention can be used successfully in such cases because they do not rely on a $T_1$ contrast, but rather on a diffusion contrast, which remains unaffected. Further, the separation problem encountered in carbonate rocks where surface relaxivity is several times lower than that for sandstone is a non-issue for ED measurements because diffusion and not surface relaxation is the dominant relaxation mechanism.

Another application of the ED measurement in accordance with the present invention is the determination of residual oil saturation (ROS). Prior art ROS measurements use a dopant, such as MnCl2, mixed with water, which mixture is injected in the borehole. The paramagnetic ions from the manganese chloride solution shorten the $T_2$ of the brine phase, causing separation between the brine and oil phases. This separation is in effect similar to the ED approach in accordance with the present invention. However, there are certain problems associated with such prior art techniques which are obviated by the use of ED measurements.

First, obviously there is no need to inject MnCl2, which results in potentially significant cost savings. Next, in the prior art approach the formation has to be drilled with an overbalance to ensure mud filtrate invasion. Invasion may not occur in low permeability zones, resulting in too high apparent oil saturations since water is also interpreted as oil. As described above, this is not a problem in ED measurements.

Another application of the ED measurements in accordance with the present invention is dealing with vugs in carbonates. Because of their large pore sizes, water filled vugs have long $T_2$'s and can easily be misinterpreted as oil. Given that $T_2$ separation is achieved, an oil-filled vug will not be misinterpreted in ED, since it will have $T_2$'s longer than the upper limit. On the other hand, the $T_2$ value from a water-filled vug will be less than the determined upper-bound value using the present invention, regardless of whether a vug is connected or disconnected. The present invention eliminates the possibility of including any water-filled vuggy porosity in the hydrocarbon volume estimation.

Further, ED measurements in accordance with the present invention are applicable in cases where the oil is more viscous. It is well known that $T_2$'s for oil decrease as the viscosity of the oil increases. Ordinarily, the separation between brine and water using, for example, DSM techniques would become more difficult for more viscous oils. However, using the ED approach in accordance with the present invention, up to a limit separation can still be maintained for high-viscosity oils by adjusting the user-controlled parameters so that Eqn. (1) holds.

In this context it should be noted that the bulk oil $T_1/T_2$ spectrum gets broader with higher viscosity. Given that $T_{20,min} <= \max(T_{2A}) <= T_{20,max}$, a portion of the oil spectrum will overlap with the water signal. Thus $T_2$'s longer than $\max(T_{2A})$ will represent only a portion of the oil signal. However, in a preferred embodiment of the present invention, given the knowledge of the oil spectrum based on laboratory measurements, the overlapping portion of the oil signal can be estimated so that an appropriate correction can be made to the hydrocarbon volume estimations. This is another important application of the method of the present invention.

c) Experimental Data

Figure 5:
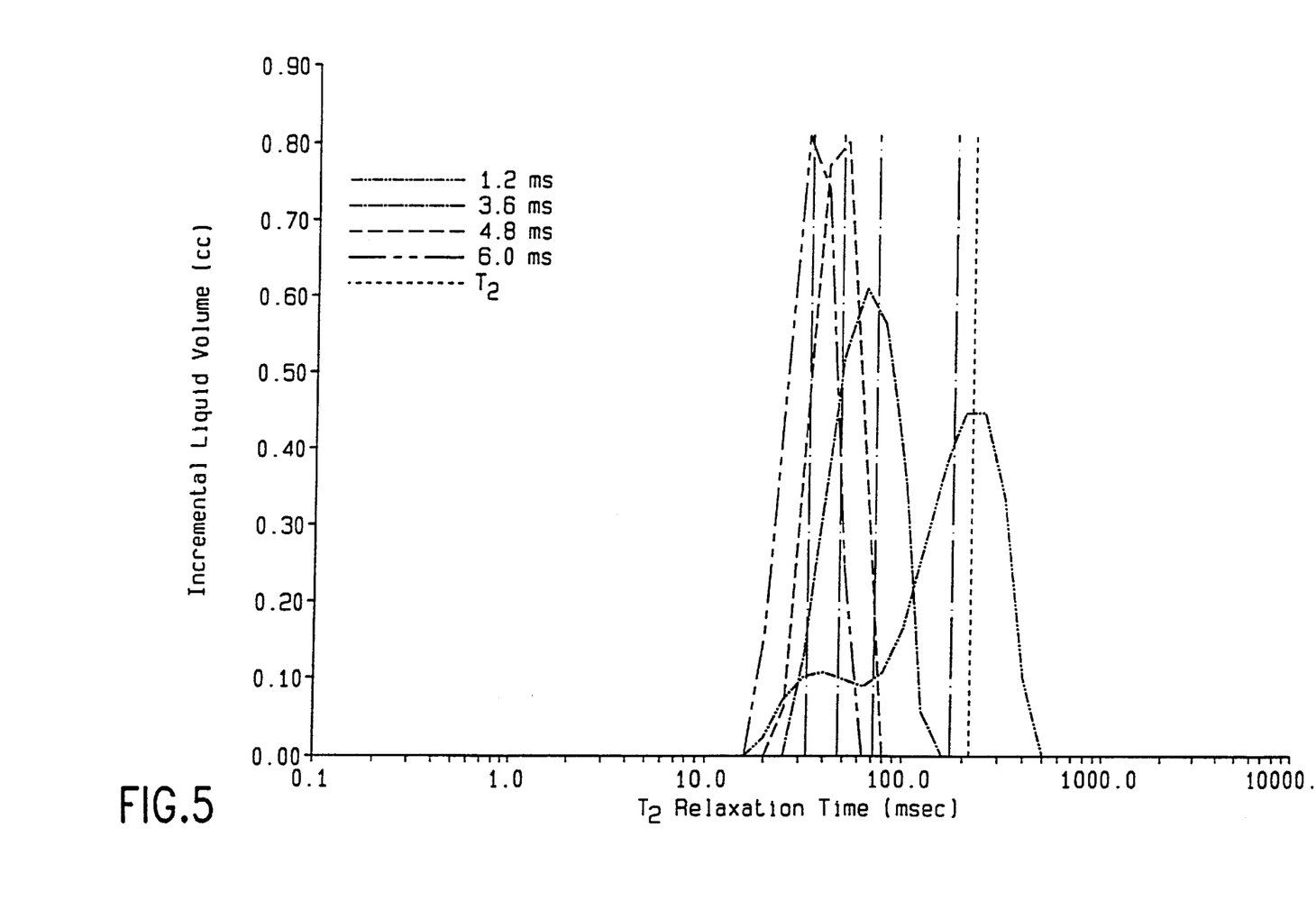
FIG. 5 is laboratory data from a Berea sandstone at 100% water saturation, illustrating the shift in the $T_2$ spectra as the inter echo time $T_E$ increases.

FIG. 5 is laboratory data from a Berea sandstone at 100% water saturation, illustrating the shift in the $T_2$ spectra as the inter echo time $T_E$ increases. The magnetic field gradient is about 17 G/cm and temperature is about 60 degrees Celsius. One can easily see the shift in the $T_2$ spectra as the inter echo time $T_E$ increases. In each case, the longest $T_2$ is shorter than the theoretically predicted $T_{2D}$ for water. This data set illustrates the concept that $\max(T_{2A})$ is predictable for water.

Figure 6:
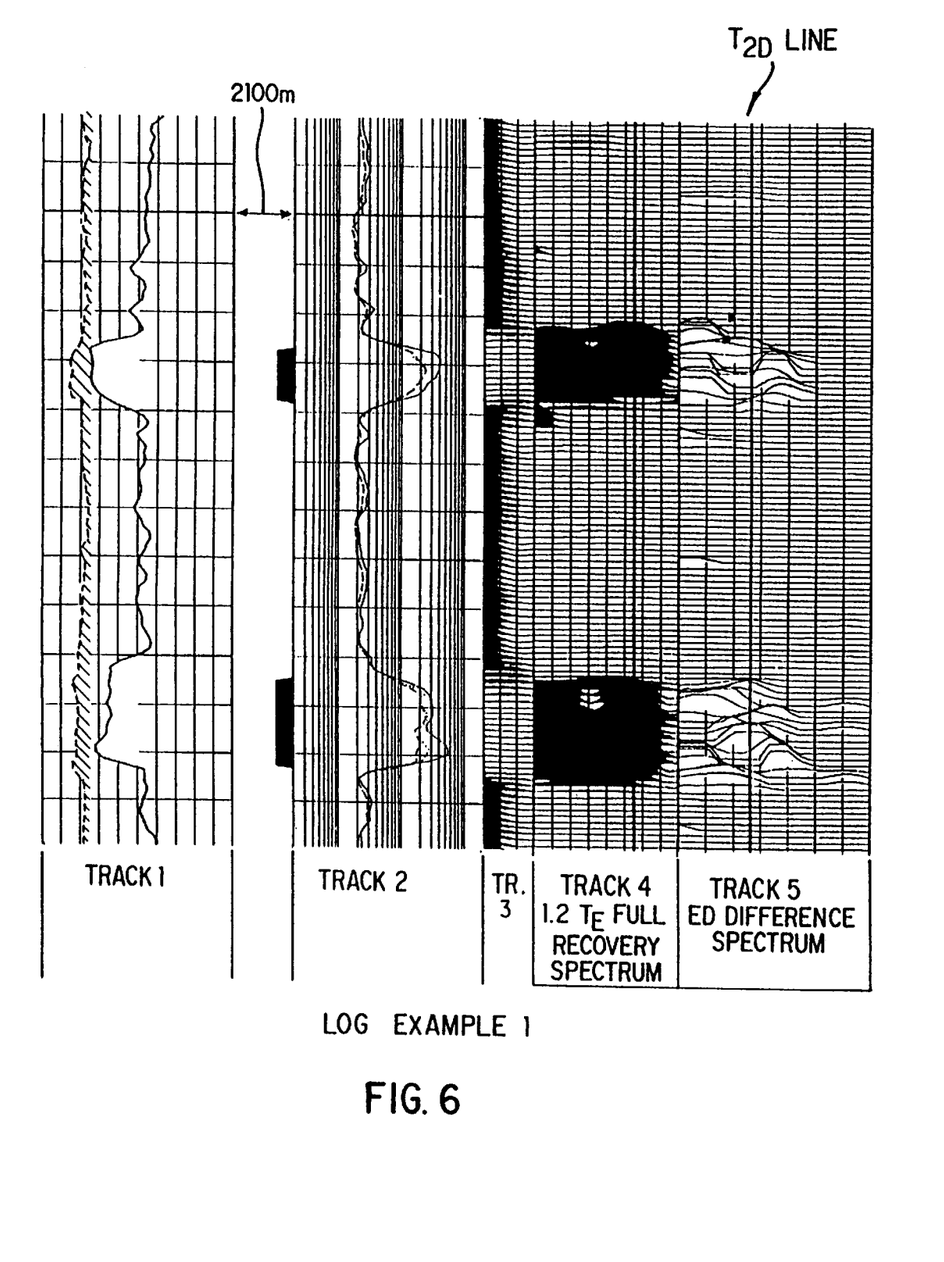
FIGS. 6 and 7 provide examples of using the enhanced diffusion method in accordance with the present invention to separate different fluid phases.
Figure 7:
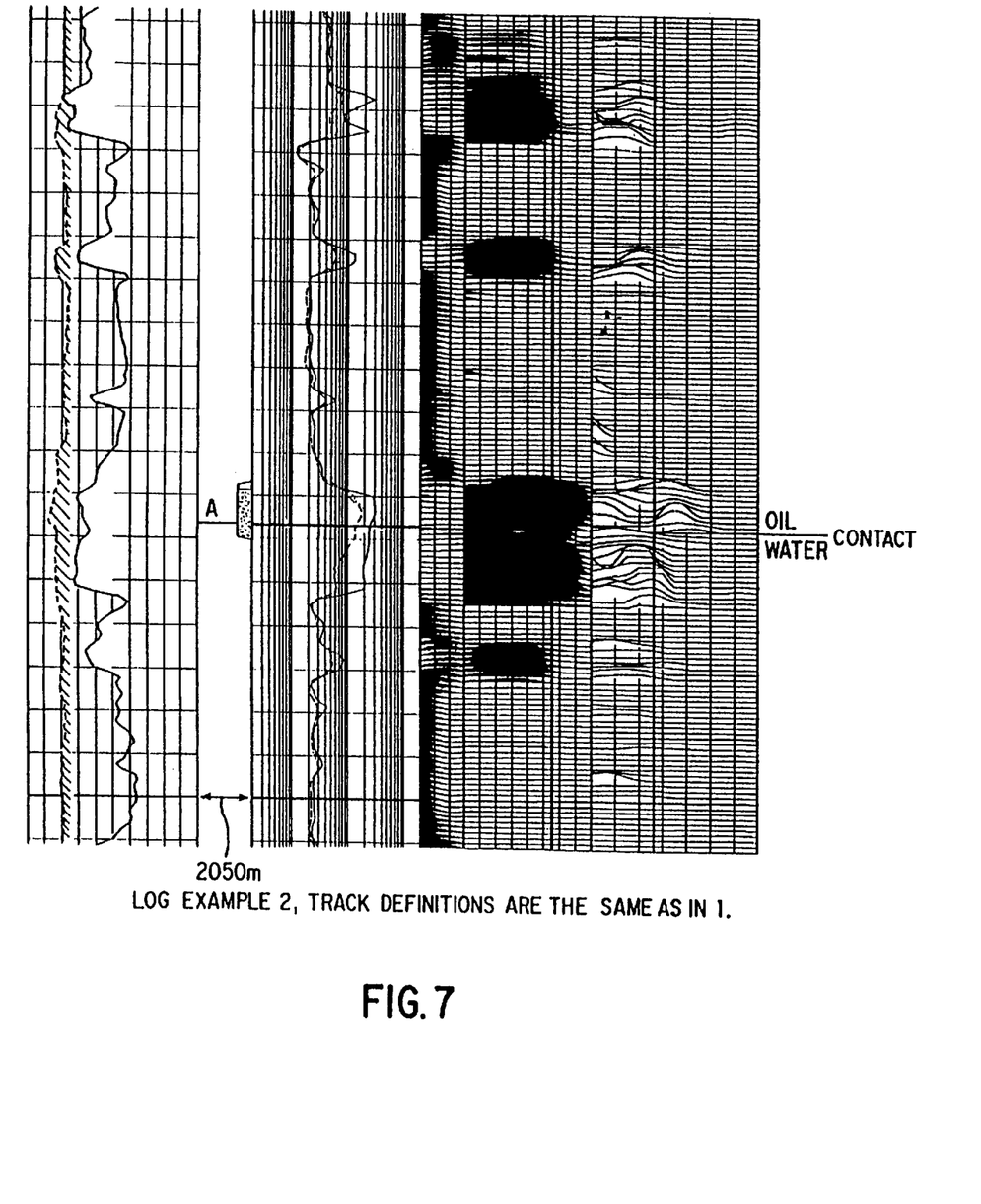

FIGS. 6 and 7 provide examples of the use of the enhanced diffusion method used in accordance with the present invention to separate different fluid phases. For the logs in both figures, the following apply GR and caliper in track 1, Resistivity in Track 2, 0.6 partial recovery $T_2$ spectra in track 3 (shaded area), 1.2 $T_E$ full recovery $T_2$ spectra in track 4 (shaded area), 3.6 $T_E$ difference spectrum (300 and 3000 ms for wait times $T_W$) from ED in track 5 (shaded area).

The perforated zones are shown in the depth track. Track 2 shading indicates oil production from the test, the shading in Track 1 indicates water with oil.

The line in the ED track 5 is the predicted $T_{2D}$ for the $T_E$, temperature and tool conditions. Any signal to the right of the line is a definite indicator of oil. If all signal is to the left of the line in Track 4, it is either all water, or water with heavy oil, which is not desirable.

EXAMPLE 1 (FIG. 6)

The two zones apparent from the marked perforations show significant signal to the right of the $T_{2D}$ line in Track 5. The interpretation from ED was good quality oil and both zones produced light oil during well tests.

Notice that there is no separation in the 1.2 $T_E$ spectra in Track 4, and that conventional DSM would show a difference due to both light oil and water.

EXAMPLE 2 (FIG. 7)

The zone of interest is the sand whose top was perforated. Data from ED difference spectrum has considerable energy to the right of the depth marked A in the depth track, indicating light oil. There is no signal to the right of the $T_{2D}$ line below this depth, indicating that there is an oil/water contact. This is proven by the well test, which produced water and oil. The well should have been perforated well above the oil/water contact, which is obvious from the ED data.

The method of the present invention was described above with reference to a $T_2$ spectral analysis. It should be understood, however, that the principles of this invention can be applied to time domain analysis techniques, as people skilled in the art will appreciate. For example, the same contrast principles can be applied in the acquisition time domain, where pairs of echo trains can be formed from the dual-$T_W$ data by matching corresponding data points, and later processed by appropriate filters. Time-domain analysis techniques for DSM that can be used by simple extension for ED measurements have been described, for example, in co-pending patent application Ser. No. 08/822,567, as well as in to Prammer et al., "Lithology-independent Gas Detection by Gradient-NMR Logging", paper SPE 30562, presented at the 69th Annual Technical Conference and Exhibition, Society of Petroleum Engineers, Dallas, Tex., Oct. 22–25, 1995, both of which are incorporated by reference.

Although the present invention has been described in connection with the preferred embodiments, it is not intended to be limited to these embodiments but rather is intended to cover such modifications, alternatives, and equivalents as can be reasonably included within the spirit and scope of the invention as defined by the following claims.

What is claimed is:

1. A method for nuclear magnetic resonance (NMR) measurements of petrophysical properties of a geologic formation comprising the steps of:

determining a set of parameters for a gradient NMR measurement, which set of parameters establishes an upper limit in the apparent transverse relaxation $T_{2A}$ of a brine phase of the formation;

obtaining a pulsed NMR log using the determined set of parameters; and estimating from the NMR log the contribution of the hydrocarbon phase as distinct from brine on the basis of the established upper limit.

2. The method of claim 1 wherein the set of determined parameters comprises the inter echo spacing $T_E$ of a pulsed NMR sequence.

3. The method of claim 2 wherein the inter echo spacing $T_E$ is determined at least on the basis of the expected viscosity of the oil in the formation.

4. The method of claim 2 wherein the interecho spacing $T_E$ is longer than about 0.3 msec.

5. The method of claim 1 wherein the set of determined parameters comprises the magnetic field gradient G of the NMR measurement.

6. The method of claim 1 wherein the upper limit in the apparent transverse relaxation $T_{2A}$ of a brine phase of the formation is established using the expression:

$$\max\{T_{2A}\} \leq T_{2D}$$

where $T_{2D}$ is the transversal relaxation time component reflecting a diffusion relaxation mechanism, which value is found using the expression:

$$T_{2D}^{-1} = \frac{D}{12}(\gamma \cdot G \cdot T_E)^2$$

where $\gamma$ is the gyromagnetic ratio ($=2\pi \times 4258$ rad/sec/Gauss for protons), D is the brine diffusion coefficient, G is the magnetic field gradient and $T_E$ is the inter echo time used in the NMR measurement.

7. The method of claim 1 wherein the step of estimating comprises the step of determining from the NMR log a distribution of transverse relaxation times.

8. The method of claim 1 further comprising the step of detecting vugs in the formation on the basis of the estimate of the hydrocarbon contribution.

9. The method of claim 1 wherein the step of estimating is done in the $T_2$ spectrum domain, regardless of $T_1$ relaxation properties of brine and hydrocarbon phases.

10. The method of claim 1, wherein the step of estimating is done in the $T_2$ spectrum domain, regardless of weaker surface relaxation property of carbonates.

11. The method of claim 1, wherein water-filled vugs are excluded from estimated hydrocarbon contributions, independent of the size of the vugs.

12. The method of claim 1, further comprising the step of obtaining residual oil saturations directly without forcing $T_2$ shortening agents into the formation.

13. The method of claim 1, further comprising the step of providing a correction to the. estimated hydrocarbon-phase contribution to account for an overlap with brine-phase contributions, using laboratory $T_2$ oil-spectrum measurements.

14. A method for separating hydrocarbons from brine in NMR measurements of a geologic formation, comprising the steps of:

determining a set of parameters for a gradient NMR measurement, which set of parameters establishes an upper limit max($T_{2A}$) in the apparent transverse relaxation of the brine;

obtaining a pulsed NMR log using the determined set of parameters; and processing the pulsed NMR log to limit the contribution of brine to components falling below the established upper limit max ($T_{2A}$).

15. The method of claim 14 wherein the set of parameters is determined so as to force diffusion as the dominant relaxation mechanism of the brine.

16. The method of claim 14 wherein the brine separation is established in the $T_2$ spectrum domain, regardless of $T_1$ relaxation properties of the brine and hydrocarbon phases.

17. The method of claim 14 wherein the upper limit max ($T_{2A}$) is obtained using the expression:

$$\max(T_{2A}) = \frac{12}{D}(\gamma \cdot G \cdot T_E)^{-2}$$

where $\gamma$ is the gyromagnetic ratio ($=2\pi \times 4258$ rad/sec/Gauss for protons), D is the self-diffusion coefficient of the brine phase, G is the magnetic field gradient and $T_E$ is the inter echo time used in the NMR measurement.

18. The method of claim 17 wherein for NMR measurements in which the magnetic field gradient in the measurement zone is characterized by a distribution of values such that Gmin<G<Gmax, the upper limit max($T_{2A}$) is computed using the expression:

$$\max(T_{2A}) = \frac{12}{D}(\gamma \cdot G_{min} \cdot T_E)^{-2}.$$

19. The method of claim 14 wherein the set of determined parameters comprises the inter echo spacing $T_E$ of a pulsed NMR sequence.

20. The method of claim 19 wherein the interecho spacing $T_E$ is determined at least on the basis of the expected viscosity of the oil in the formation.

21. The method of claim 19 wherein the interecho spacing $T_E$ is longer than about 0.3 msec.

22. An apparatus for measuring petrophysical properties of a geologic formation, comprising:

a probe adapted to be deployed in a borehole, the probe capable of generating a gradient magnetic field and of imparting one or more pulsed NMR sequences having predetermined parameters in said formation;

means for determining an upper limit $\max(T_{2A})$ in the apparent transverse relaxation of a brine phase of said formation; and means for estimating the contribution of a hydrocarbon phase of said formation on the basis of said upper limit $\max(T_{2A})$ and a NMR log obtained using said gradient magnetic field and said one or more pulsed NMR sequences.

23. The apparatus of claim 22 wherein the upper limit in the apparent transverse relaxation $T_{2A}$ of the brine phase of the formation is determined using the expression:

$$\max\{T_{2A}\} \leq T_{2D}$$

where $T_{2D}$ is the transversal relaxation time component reflecting a diffusion relaxation mechanism, which value is found using the expression:

$$T_{2D}^{-1} = \frac{D}{12}(\gamma \cdot G \cdot T_E)^2$$

where $\gamma$ is the gyromagnetic ratio ($=2\pi \times 4258$ rad/sec/Gauss for protons), D is the brine diffusion coefficient, G is the magnetic field gradient and $T_E$ is the interecho time used in the NMR measurement.

24. The apparatus of claim 23 wherein said means for determining an upper limit provides input to a pulse programmer capable of varying the inter echo time $T_E$ of said one or more pulsed NMR sequences.

25. The apparatus of claim 23 wherein said means for determining an upper limit provides input to a means for varying the magnetic field gradient G generated by the probe.

26. An apparatus for measuring petrophysical properties of a geologic formation, comprising:

a NMR measurement probe adapted to be deployed in a borehole, the probe being capable of generating a gradient magnetic field in the formation, and having one or more antennas for transmitting into and receiving from the formation of NMR signals;

means for determining an upper limit $\max(T_{2A})$ in the apparent transverse relaxation of a brine phase of said formation; and a controller for setting measurement parameters for the probe, which are based on the determined upper limit; and a computer processor for separating the contribution of the brine phase from hydrocarbons on the basis of the received NMR signals and the determined upper limit.

27. The apparatus of claim 26 wherein said controller comprises a pulse programmer capable of varying the interecho time $T_E$ of said one or more pulsed NMR sequences.

* * * * *